United States Patent
Hsu et al.

(10) Patent No.: US 10,905,876 B2
(45) Date of Patent: Feb. 2, 2021

(54) ELECTRICAL STIMULATION CONTROL CIRCUIT AND CONTROL METHOD THEREOF

(71) Applicants: Industrial Technology Research Institute, Hsinchu (TW); KAOHSIUNG MEDICAL UNIVERSITY, Kaohsiung (TW)

(72) Inventors: Chia-Chan Hsu, Tainan (TW); Chao-Jen Huang, Hsinchu County (TW); Su-Shin Lee, Kaohsiung (TW)

(73) Assignees: INDUSTRIAL TECHNOLOGY RESEARCH INSTITUTE, Hsinchu (TW); KAOHSIUNG MEDICAL UNIVERSITY, Kaohsiung (TW)

( * ) Notice: Subject to any disclaimer, the term of this patent is extended or adjusted under 35 U.S.C. 154(b) by 316 days.

(21) Appl. No.: 15/857,361

(22) Filed: Dec. 28, 2017

(65) Prior Publication Data

US 2019/0184157 A1 Jun. 20, 2019

Related U.S. Application Data

(60) Provisional application No. 62/598,597, filed on Dec. 14, 2017.

(51) Int. Cl.
*A61N 1/32* (2006.01)
*A61N 1/36* (2006.01)
*A61N 1/04* (2006.01)

(52) U.S. Cl.
CPC .......... *A61N 1/328* (2013.01); *A61N 1/0468* (2013.01); *A61N 1/323* (2013.01); *A61N 1/326* (2013.01);

(Continued)

(58) Field of Classification Search
CPC .... A61N 1/328; A61N 1/3603; A61N 1/0468; A61N 1/323
See application file for complete search history.

(56) References Cited

U.S. PATENT DOCUMENTS

| 7,039,468 B2 | 5/2006 | Freed et al. |
| 8,478,412 B2 | 7/2013 | Ignagni et al. |

(Continued)

FOREIGN PATENT DOCUMENTS

| CN | 104001265 | 8/2014 |
| CN | 105492067 A | 4/2016 |

(Continued)

OTHER PUBLICATIONS

Taiwan Patent Office, Office Action, Patent Application Serial No. 106146228, dated Aug. 1, 2018, Taiwan.

(Continued)

*Primary Examiner* — Joseph M Dietrich

(57) ABSTRACT

An electrical stimulation control circuit including a pulse generator, a processing circuit and an electrode is provided. The pulse generator is configured to generate a switching signal. The processing circuit generates an energy signal according to the switching signal. The electrode is configured to contact the skin of a living body and includes a first comb electrode and a second comb electrode. The first comb electrode receives the energy signal and includes a plurality of first electrodes. The first electrodes are electrically connected to each other and extended along a first direction. The second comb electrode receives a ground signal and includes a plurality of second electrodes. The second electrodes are electrically connected to each other and extended along a second direction opposite to the first direction. The first electrodes and the second electrodes are arranged in a staggered manner and electrically insulated from each other.

15 Claims, 7 Drawing Sheets

(52) U.S. Cl.
CPC ....... *A61N 1/3603* (2017.08); *A61N 1/36017* (2013.01); *A61N 1/0476* (2013.01); *A61N 1/36034* (2017.08)

(56) References Cited

U.S. PATENT DOCUMENTS

| | | | |
|---|---|---|---|
| 8,676,323 | B2 | 3/2014 | Ignagni et al. |
| 8,788,055 | B2 | 7/2014 | Gerber et al. |
| 8,906,006 | B2 | 12/2014 | Chornenky et al. |
| 8,977,370 | B2 | 3/2015 | Colthurst |
| 9,204,822 | B2 | 12/2015 | Lane et al. |
| 9,352,157 | B2 | 5/2016 | Tang |
| 9,643,006 | B2 | 5/2017 | Bachinski et al. |
| 9,656,086 | B2 | 5/2017 | Mika et al. |
| 2010/0298720 | A1* | 11/2010 | Potkay ............. A61B 5/0215 600/485 |
| 2015/0025598 | A1 | 1/2015 | Kang et al. |
| 2016/0099582 | A1 | 4/2016 | Ramorini et al. |
| 2016/0101284 | A1* | 4/2016 | Bachinski ........... A61N 1/323 607/46 |

FOREIGN PATENT DOCUMENTS

| | | |
|---|---|---|
| EP | 2392381 | 7/2016 |
| TW | I235673 | 7/2005 |
| TW | 200822942 | 6/2008 |
| TW | I562799 | 12/2016 |
| TW | I581771 | 5/2017 |
| TW | M541866 | 5/2017 |
| TW | I594786 | 8/2017 |
| TW | M560926 | 6/2018 |
| WO | WO 2005067792 | 7/2005 |
| WO | WO 2015186087 | 12/2015 |

OTHER PUBLICATIONS

Santa C. Huerta et al., "A Universal Functional Electrical Stimulator Based on Merged Flyback-SC Circuit", 15th International Power Electronics and Motion Control Conference (EPE/PEMC), Sep. 2012, pp. LS5a.3-1-LS5a.3-5, IEEE, US.

Gwo-Ching Chang et al., "A Microprocessor-based Multichannel Subsensory Stochastic Resonance Electrical Stimulator," IEEE Engineering in Medicine and Biology Society (EMBC), Jul. 2013, pp. 3559-3562, IEEE, US.

Wei Xin et al., "A Programmable Electrical Stimulator for Suppressing Pathological Tremor," World Congress on Intelligent Control and Automation (WCICA), Jun. 2016, pp. 1669-1674, IEEE, US.

Jirawat Jitprasutwit et al., "Development and Distribution of Functional Electrical Stimulator for Foot Drop for Thais," The 2015 Biomedical Engineering International Conference (BMEiCON), Nov. 2015, 4 pages, IEEE, US.

Muhammad Awais Bin Altaf et al., "A 2.45uW Patient-Specific Non-invasive Transcranial Electrical Stimulator with an Adaptive Skin-Electrode Impedance Monitor," IEEE Biomedical Circuits and Systems Conference (BioCAS), Oct. 2015, 4 pages, IEEE, US.

Ashley M. Stewart et al., "Design and Testing of a Novel, Low-cost, Low-voltage, Functional Electrical Stimulator," IEEE/ASME International Conference on Mechatronic and Embedded Systems and Applications (MESA), Oct. 2016, 6 pages, IEEE, US.

Hai-Peng Wang et al., "Design of a Pulse-Triggered Four-Channel Functional Electrical Stimulator Using Complementary Current Source and Time Division Multiplexing Output Method," IEEE Engineering in Medicine and Biology Society (EMB) Aug. 2015, pp. 1671-1674, IEEE, US.

Reza Ranjandish et al., "A Low-Power Digitally Closed-Loop Electrical Stimulator Suited for Low-Pulse-Width-Stimulation," 2015 $23^{rd}$ Iranian Conference on Electrical Engineering, May 2015, pp. 1393-1397, IEEE, US.

Qi Xu et al., "A programmable multi-channel stimulator for array electrodes in transcutaneous electrical stimulation," 2011 IEEE/ICME International Conference on Complex Medical Engineering, May 2011, pp. 652-656, IEEE, US.

Sara Ud-Din et al., "Electrical Stimulation and Cutaneous Wound Healing: A Review of Clinical Evidence Healthcare," Healthcare, Oct. 2014, pp. 445-467, vol. 2, NCBI, US.

Jaideep Banerjee et al., "Improvement of Human Keratinocyte Migration by a Redox Active Bioelectric Dressing," Bioelectric Dressing Mediated Cell Migration, Mar. 2014; pp. 1-14, vol. 9; Issue 3, PLOS ONE, US.

Hosan Kim et al., "An Overview of the Efficacy of a Next Generation Electroceutical Wound Care Device," Military Medicine, May 2016, pp. 184-190, vol. 181, Association of Military Surgeons of the U.S., US.

S.S. Park al., "Measurement of microelectric potentials in a bioelectrically-active wound care device in the presence of bacteria," Journal of Wound Care, Jan. 2015, pp. 23-33, vol. 24, No. 1, MA Healthcare Ltd, UK.

Atit Tanntrakarn et al., "A Portable Switching Bi-Phasic Stimulator with Level-Shifting Inverter for Functional Electrical Stimulation operating under a 6V Supply Voltage," TENCON 2015 IEEE Region 10 Conference, Nov. 2015, 4 pages, IEEE, US.

* cited by examiner

ELECTRICAL STIMULATION CONTROL CIRCUIT AND CONTROL METHOD THEREOF

FIELD OF THE INVENTION

The present disclosure relates to a control circuit, and more particularly to a control circuit that applies electrical stimulation to activate skin regeneration.

BACKGROUND

When a human body experiences physical trauma, a wound often remains on the surface of the skin. Some conventional methods of treating a wound are to bind a bandage over the wound, put a dressing on the wound, or attach artificial skin to the wound. However, these conventional treatment methods are time-consuming and expensive.

SUMMARY

In accordance with an embodiment, an electrical stimulation control circuit comprises a pulse generator, a processing circuit and an electrode. The pulse generator is configured to generate a switching signal. The processing circuit generates an energy signal according to the switching signal. The electrode is configured to contact the skin of a living body and comprises a first comb electrode and a second comb electrode. The first comb electrode receives the energy signal and comprises a plurality of first electrodes. The first electrodes are electrically connected to each other and extend in a first direction. The second comb electrode receives a ground voltage and comprises a plurality of second electrodes. The second electrodes are electrically connected to each other and extend in a second direction opposite to the first direction. The first electrodes and the second electrodes are arranged in a staggered manner and are electrically insulated from each other.

In accordance with a further embodiment, a control method for stimulating skin cells of a living body comprises generating a switching signal; generating an energy signal according to the switching signal; and transmitting the energy signal to the skin of the living body via an electrode. The electrode comprises a first comb electrode and a second comb electrode. The first comb electrode receives the energy signal and comprises a plurality of first electrodes. The first electrodes are electrically connected to each other and extend in a first direction. The second comb electrode receives a ground voltage and comprising a plurality of second electrodes. The second electrodes are electrically connected to each other and extend in a second direction opposite to the first direction. The first electrodes and the second electrodes are arranged in a staggered manner and are electrically insulated from each other.

BRIEF DESCRIPTION OF THE DRAWINGS

The present disclosure can be more fully understood by referring to the following detailed description and examples with references made to the accompanying drawings, wherein.

DETAILED DESCRIPTION OF THE INVENTION

Figure 1A:
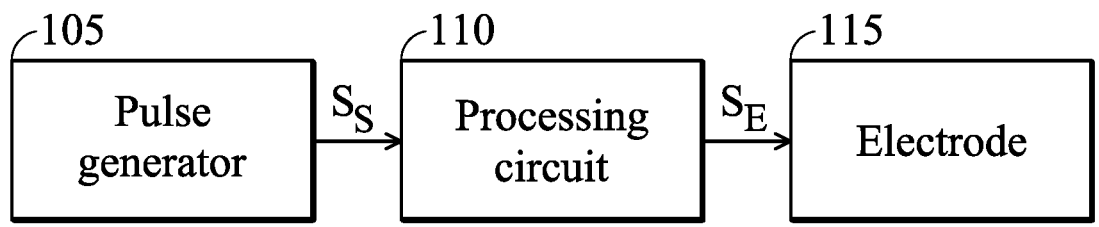
FIG. 1A is a schematic diagram of an exemplary embodiment of an electrical stimulation control circuit according to various aspects of the present disclosure.

The present disclosure will be described with respect to particular embodiments and with reference to certain drawings, but the present disclosure is not limited thereto and is only limited by the claims. The drawings described are only schematic and are non-limiting. In the drawings, the size of some of the elements may be exaggerated for illustrative purposes and not drawn to scale. The dimensions and the relative dimensions do not correspond to actual dimensions in the practice of the present disclosure.

FIG. 1A is a schematic diagram of an exemplary embodiment of an electrical stimulation control circuit according to various aspects of the present disclosure. As shown in FIG. 1A, the electrical stimulation control circuit 100A comprises a pulse generator 105, a processing circuit 110 and an electrode 115. The pulse generator 105 is configured to generate a switching signal $S_S$. In one embodiment, the pulse generator 105 adjusts the frequency of the switching signal $S_S$ and the duty-cycle of the switching signal $S_S$ according to a set signal (not shown).

In the disclosure, the internal circuit structure of the pulse generator 105 is not limited. In one embodiment, the pulse generator 105 comprises an analog circuit (not shown) and a comparing circuit (not shown). The analog circuit is configured to generate a triangle wave or a sawtooth wave. The comparing circuit compares the triangle wave or the sawtooth wave with a reference signal to generate a square wave. In this case, the square wave serves as the switching signal $S_S$.

The processing circuit 110 generates an energy signal $S_E$ according to the switching signal $S_S$. In one embodiment, when the switching signal $S_S$ is at a first level, the processing circuit 110 sets the energy signal $S_E$ to equal to a first voltage. When the switching signal $S_S$ is at a second level, the energy signal $S_E$ is set to equal to a second voltage. In this embodiment, the first voltage is higher than the second voltage. In one embodiment, the second voltage is a ground voltage, such as 0V. In addition, the first level is opposite to the second level. When the first level is at a high level, the second level is at a low level. When the first level is at the low level, the second voltage is at the high level.

The electrode 115 is configured to contact the skin of a living body. The type of electrode 115 is not limited in the disclosure. In one embodiment, the electrode 115 is a thermoelectric dressing electrode. In this embodiment, when the electrode 115 receives the energy signal $S_E$, the electrode 115 applies a low strength voltage to the skin of the living body to activate the regeneration capability of the skin cells and reduce the trauma range of the skin. The number of electrode 115 is not limited in the present disclosure. In other embodiments, the electrical stimulation control circuit 100A may comprise more electrodes. In this case, the processing circuit 110 may provide the same or different energy signals to different electrodes.

Figure 1B:
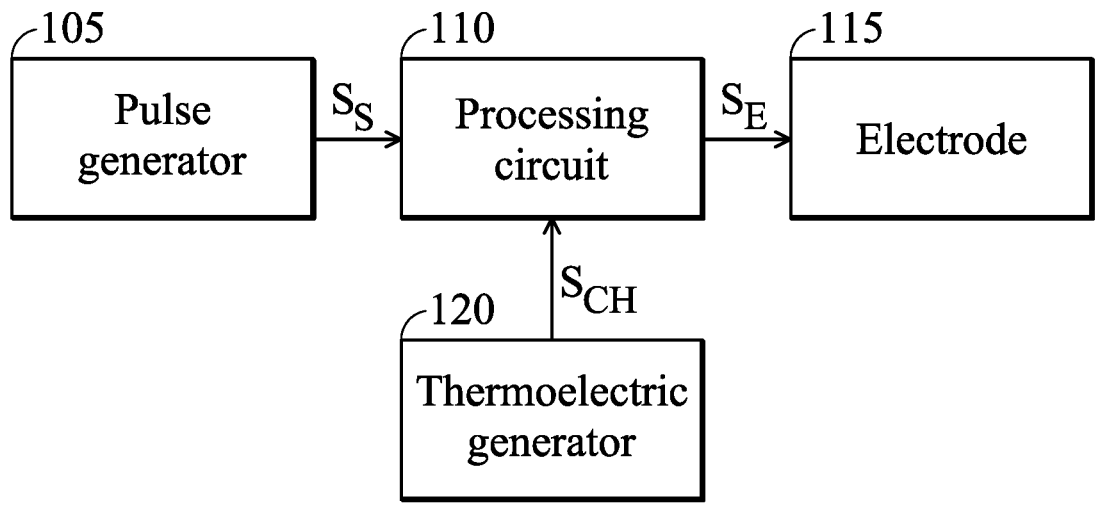
FIG. 1B is a schematic diagram of another exemplary embodiment of the electrical stimulation control circuit according to various aspects of the present disclosure.

FIG. 1B is a schematic diagram of another exemplary embodiment of the electrical stimulation control circuit according to various aspects of the present disclosure. FIG. 1B is similar to FIG. 1A except that the electrical stimulation control circuit 100B further comprises a thermoelectric generator 120. In this embodiment, the thermoelectric generator 120 contacts the skin of the living body and acquires energy according to the body temperature of the living body to generate a charge signal $S_{CH}$. In one embodiment, the power circuit 110 charges an energy storage element (not shown) disposed in the power circuit 110 according to the charge signal $S_{CH}$.

Figure 2A:
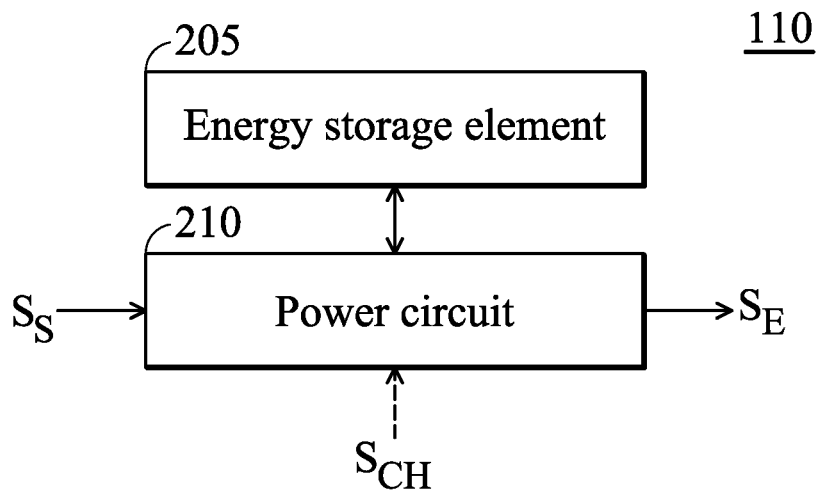
FIG. 2A is a schematic diagram of an exemplary embodiment of a processing circuit according to various aspects of the present disclosure.

FIG. 2A is a schematic diagram of an exemplary embodiment of a processing circuit according to various aspects of the present disclosure. As shown in FIG. 2A, the processing circuit 110 comprises an energy storage element 205 and a power circuit 210. The energy storage element 205 is configured to store energy. The type of energy storage element 205 is not limited in the disclosure. In one embodiment, the energy storage element 205 is a lithium ion capacitor, a super-capacitor or a battery.

The power circuit 210 acquires the energy from the energy storage element 205 according to the switching signal $S_S$ to generate the energy signal $S_E$. In one embodiment, the power circuit 210 further charges the energy storage element 205 according to the switching signal $S_S$. In another embodiment, the power circuit 210 charges the energy storage element according to the charge signal $S_{CH}$.

In the disclosure, the circuit structure of the power circuit 210 is not limited. In one embodiment, the power circuit 210 comprises a single-inductor multiple-input-multiple-output circuit. In other embodiments, the power circuit 210 is a DC-to-DC converter. For example, the power circuit 210 may be a buck converter, a boost converter, a flyback converter or a low drop voltage regulator.

Figure 2B:
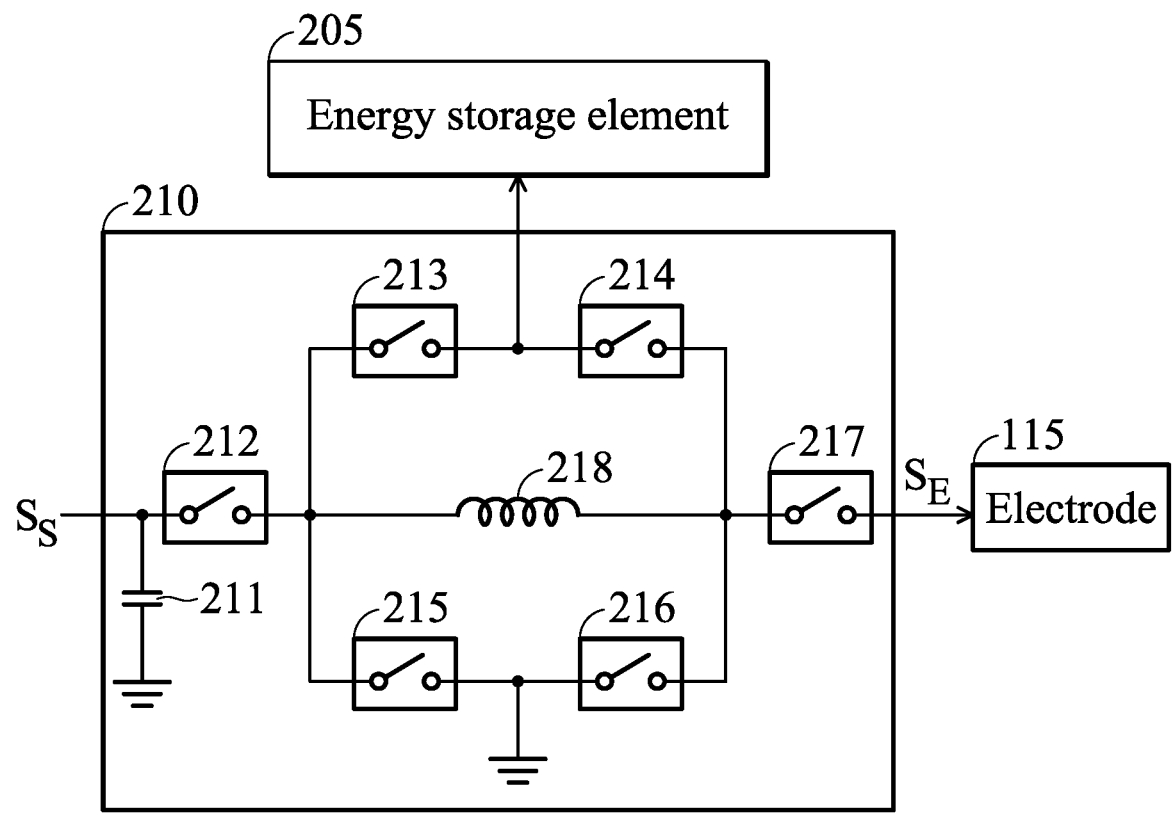
FIG. 2B is a schematic diagram of an exemplary embodiment of a power circuit according to various aspects of the present disclosure.

FIG. 2B is a schematic diagram of an exemplary embodiment of a power circuit according to various aspects of the present disclosure. As shown in FIG. 2B, the power circuit 210 comprises a capacitor 211, switches 212~217 and an inductor 218. When the switches 212 and 216 are turned on and the switch 212 receives the switching signal $S_S$, a current flows through the switch 212, the inductor 218, and the switch 216 to ground. At this time, the inductor 218 stores energy. When the switches 215 and 217 are turned on, a current flows from ground and through switch 215, the inductor 218, and the switch 214 to the energy storage element 205. Therefore, the energy stored in the inductor 218 is transferred to the energy storage element 205 and the energy storage element 205 is charged. The type of switches 212~217 are not limited in the present disclosure. In one embodiment, the switches 212~217 are transistors, such as metal-oxide-semiconductor field effect transistor (MOSFET). One terminal of the switch 212 receives the switching signal $S_S$. The other terminal of the switch 212 is simultaneously coupled to the switch 213, the inductor 218 and the switch 215. The other terminal of the switch 215 is coupled to the switch 216 and ground. One terminal of the switch 217 transmits the energy signal $S_E$ to the electrode 115, the other terminal of the switch 217, the switch 214, the inductor 218 and the switch 216.

In this embodiment, the inductor 218 is configured to store and release energy to achieve an energy transfer effect. For example, when the current passing through the inductor 218 is increased, the inductor 218 stores energy. When the current passing through the inductor 218 is reduced, the inductor 218 releases energy. In one embodiment, the inductor 218 releases energy to the electrode 115 or the energy storage element 205.

Figure 2C:
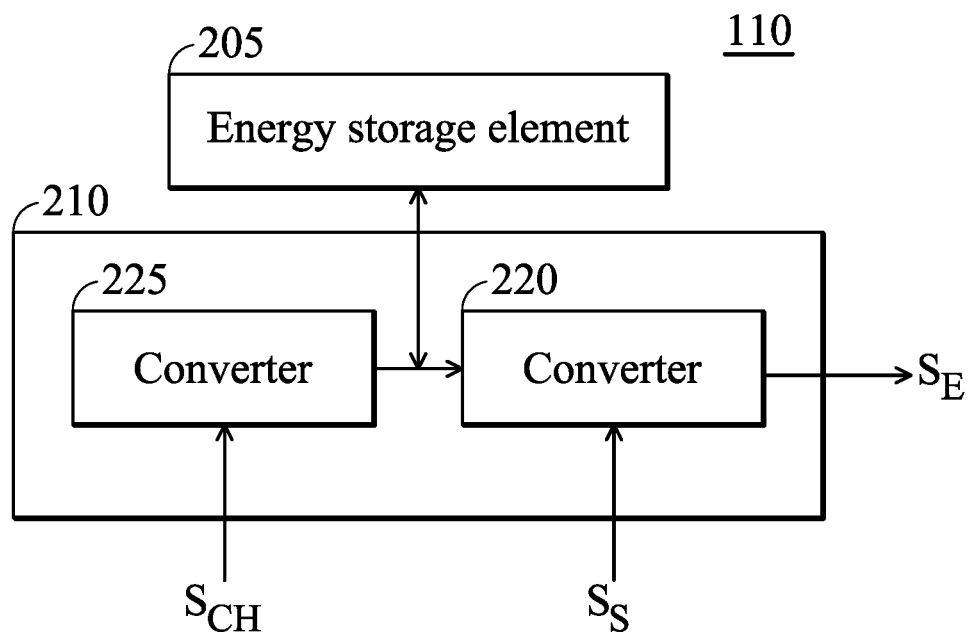
FIG. 2C is a schematic diagram of another exemplary embodiment of the processing circuit according to various aspects of the present disclosure.

FIG. 2C is a schematic diagram of another exemplary embodiment of the processing circuit according to various aspects of the present disclosure. In this embodiment, the power circuit 210 comprises converters 225 and 220. The converter 225 charges the energy storage element 205 according to the charge signal $S_{CH}$. The converter 220 acquires the energy from the energy storage element 205 according to the switching signal $S_S$ to generate the energy signal $S_E$. In the present disclosure, the circuit structures of converters 225 and 220 are not limited. In one embodiment, at least one of the converters 225 and 220 is a DC-to-DC converter. For example, at least one of the converters 225 and 220 comprises a buck converter, a boost converter, a flyback converter or a low drop voltage regulator.

Figure 2D:
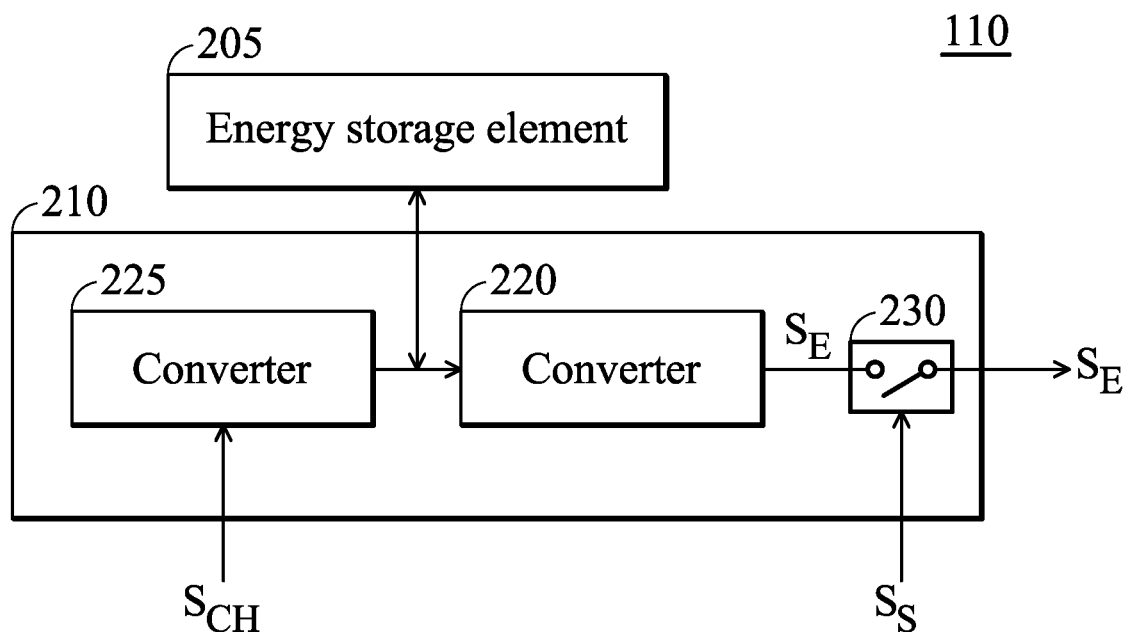
FIG. 2D is a schematic diagram of another exemplary embodiment of the processing circuit according to various aspects of the present disclosure.

FIG. 2D is a schematic diagram of another exemplary embodiment of the processing circuit according to various aspects of the present disclosure. In this embodiment, the power circuit 210 comprises converters 225 and 220 and a switch 230. The converter 225 charges the energy storage element 205 according to the charge signal $S_{CH}$. The converter 220 acquires the energy stored in the energy storage element 205 to generate the energy signal $S_E$. The switch 230 is coupled between the converter 220 and electrode 115 and determines whether to transmit the energy signal $S_E$ generated by the converter 220 to the electrode 115 according to the energy signal $S_E$. The type of the switch 230 is not limited in the present disclosure. In one embodiment, the switch 230 is a P-type transistor or an N-type transistor.

Figure 3:
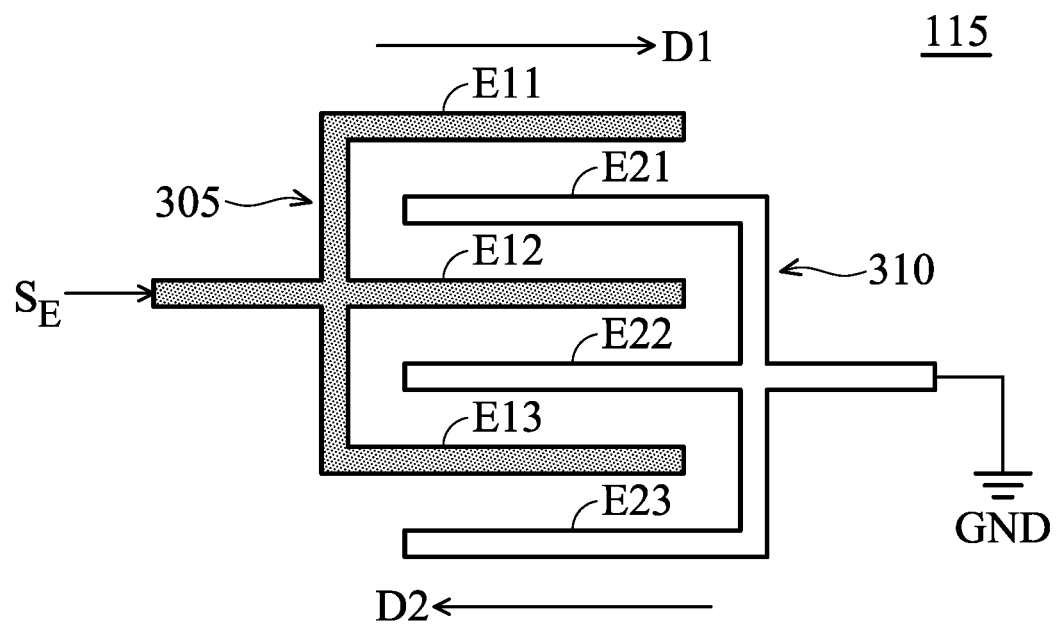
FIG. 3 is a schematic diagram of an exemplary embodiment of an electrode according to various aspects of the present disclosure.

FIG. 3 is a schematic diagram of an exemplary embodiment of an electrode according to various aspects of the present disclosure. In this embodiment, the electrode 115 comprises comb electrodes 305 and 310. The comb electrode 305 receives the energy signal $S_E$ and comprises electrodes E11~E13. The electrodes E11~E13 are electrically connected to each other and extend in a direction D1. The number of electrodes is not limited in the disclosure. In some embodiments, the comb electrode 305 may comprise more electrodes or fewer electrodes.

Additionally, the comb electrode 310 receives a ground voltage GND and comprises electrodes E21~E23. The electrodes E21~E23 are electrically connected to each other and extend in a direction D2. In this embodiment, the direction D1 is opposite to the direction D2. The electrodes E11~E13 and E21~E23 are arranged in a staggered manner and are electrically insulated from each other. The number of electrodes is not limited in the present disclosure. In other embodiments, the comb electrode 310 comprises only two electrodes or more electrodes.

When the electrode 115 is attached to the skin of a living body, if the comb electrode 305 receives the energy signal $S_E$ and the comb electrode 310 receives the ground voltage GND, a current passes from the comb electrode 310, through the skin of the living body and to the comb electrode 305. The strength of the current relates the number of electrodes E11~E13 and E21~E23. In this embodiment, the number of electrodes of the comb electrode 305 or 310 is 3. When the comb electrodes 305 and 310 comprise more electrodes, the current passing through the comb electrodes 305 and 310 is large. Furthermore, the current passing through the comb electrodes 305 and 310 also relates to the energy signal $S_E$. When the voltage of the energy signal $S_E$ is strong, the current passing through the comb electrodes 305 and 310 is large. In one embodiment, the distance between the electrodes E11 and E21 is about 100 μm. In one embodiment, the distance between the electrodes E11 and E21 is about 10 μm to about 300 μm. In one embodiment, the electrode 115 is attached to the wound of a human. In this case, the electrical stimulation is applied to the electrode 115 to increase the regeneration capability of the skin cells.

Figure 4:
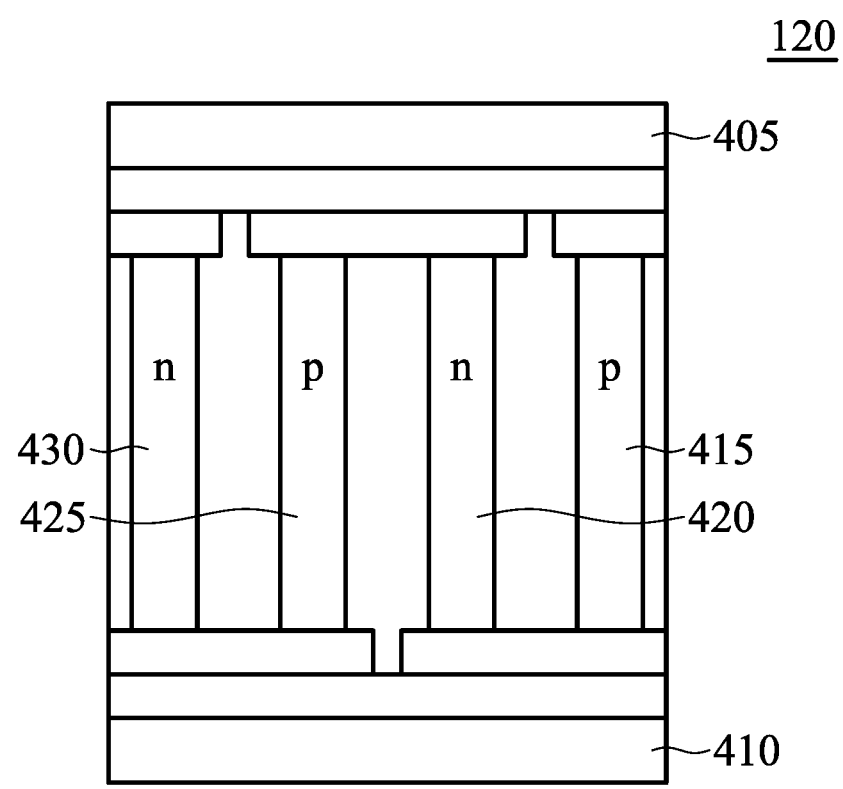
FIG. 4 is a schematic diagram of an exemplary embodiment of a thermoelectric generator according to various aspects of the present disclosure.

FIG. 4 is a schematic diagram of an exemplary embodiment of a thermoelectric generator according to various aspects of the present disclosure. The thermoelectric generator 120 comprises a first terminal 405, a second terminal 410, p-type semiconductor materials 415 and 425 and n-type semiconductor materials 420 and 430. When the second terminal 410 contacts a living body, the temperature of the second terminal 410 is gradually increased. When the temperature difference between the second terminal 410 and the first terminal 405 reaches a predetermined value, the holes in the p-type semiconductor materials 415 and 425 are moved toward a cold terminal (e.g. the first terminal 405). At this time, the electrons in the n-type semiconductor materials 420 and 430 are moved toward a hot terminal (e.g. the second terminal 410). Therefore, a current passes between the first terminal 405 and the second terminal 410, wherein the current is provided to the charge signal $S_{CH}$. In the real operation, the difference between the body temperature of a living body and the environment temperature causes the temperature difference between the cold terminal and the hot terminal of the thermoelectric generator 120 to generate a current. After the power circuit 210 transfers the current, the transferred current serves as energy to charge an energy storage element or to be provided to the electrode 115. Since the thermoelectric generator 120 utilizes the energy of the living body to charge the energy storage element (such as a battery), the electrical stimulation control circuit 100B is not limited by the capability of the battery. Therefore, the electrical stimulation control circuit 100B is capable of providing power by itself and operating normally.

Figure 5A:
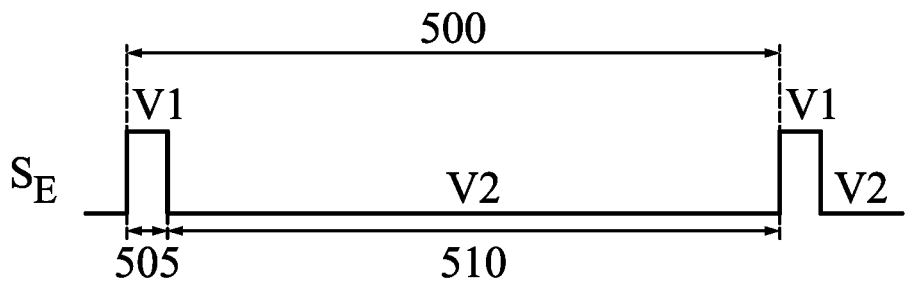
FIGS. 5A-5C are schematic diagrams of exemplary embodiments of energy signal according to various aspects of the present disclosure.

FIG. 5A is a schematic diagram of an exemplary embodiment of an energy signal according to various aspects of the present disclosure. For brevity, FIG. 5A only shows the voltage change of the energy signal $S_E$ in a cycle 500, but the disclosure is not limited thereto. In other embodiment, the voltage changes of the energy signal $S_E$ in other periods are the same as the voltage change of the energy signal $S_E$ in the cycle 500.

As shown in FIG. 5A, the energy signal $S_E$ is equal to a voltage V1 in the period 505. In the period 510, the energy signal $S_E$ is equal to a voltage V2. The voltage V1 is higher than the voltage V2. In one embodiment, the voltage V2 is equal to a ground voltage, a positive voltage higher than 0V, a minimum voltage utilized in the processing circuit 110.

The durations of the periods 505 and 510 are not limited in the present disclosure. In one embodiment, the duration of the period 505 is 15 minutes, and the duration of the period 510 is between 2.5 hours and 24 hours.

Figure 5B:
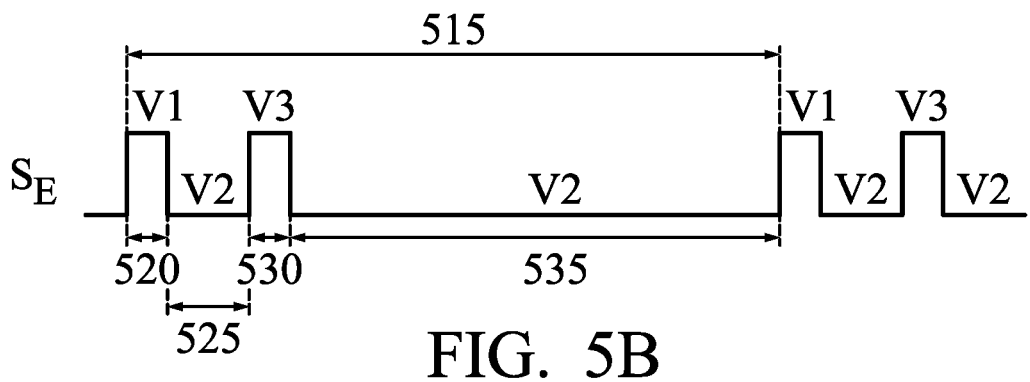

In this embodiment, the energy signal $S_E$ only has a single positive pulse in the cycle 500. In other embodiments, the number of positive pulses of the energy signal $S_E$ is greater than 2. As shown in FIG. 5B, the energy signal $S_E$ has two positive pulses in the cycle 515. The energy signal $S_E$ is equal to the voltage V1 in the period 520. The energy signal $S_E$ is equal to the voltage V3 in the period 530. The voltage V3 may be equal to, higher than, or lower than the voltage V1. Additionally, the duration of the period 520 may be the same as or different from the duration of the period 530. In one embodiment, the durations of the periods 520 and 530 are 15 minutes.

In the periods 525 and 530, the energy signal $S_E$ is equal to the voltage V2. In one embodiment, the duration of the period 525 is about 2.5 hours and the duration of the period 535 is about 24 hours, but the disclosure is not limited thereto. In some embodiments, the durations of the periods 525 and 535 are between 2.5 hours and 24 hours.

Figure 5C:
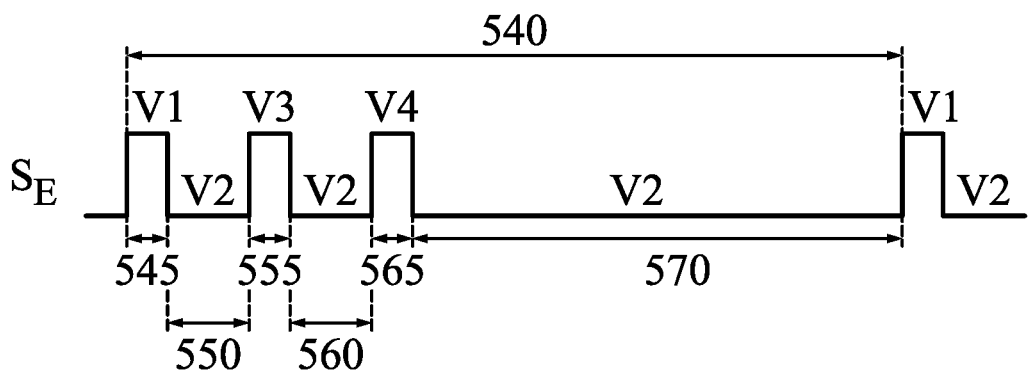

In FIG. 5C, the energy signal $S_E$ has three positive pulses in the cycle 540. In the period 545, the energy signal $S_E$ is equal to the voltage V1. In the period 555, the energy signal $S_E$ is equal to the voltage V3. In the period 565, the energy signal $S_E$ is equal to the voltage V4. In one embodiment, the voltages V1, V3 and V4 are the same, but the disclosure is not limited thereto. In some embodiments, one of the voltages V1, V3 and V4 is different from another of the voltages V1, V3 and V5. Furthermore, the durations of the periods 545, 555 and 565 are not limited in the present disclosure. In one embodiment, the durations of the periods 545, 555 and 565 are equal to 15 minutes. In other embodiments, one duration of the periods 545, 555 and 565 may be different from another duration of the periods 545, 555 and 565.

In the periods 550, 560 and 570, the energy signal $S_E$ is equal to the voltage V2. In one embodiment, the duration of the periods 550 and 560 are equal to 2.5 hours, and the duration of the period 570 is 24 hours, but the disclosure is not limited thereto. In other embodiments, the durations of the periods 550, 560 and 570 are between 2.5 hours and 24 hours.

In the present disclosure, the voltages V1, V3 and V4 are not limited. In one embodiment, when the electrode 115 is attached to the skin and the voltages V1, V3 and V4 are applied to the electrode 115, a current passes from the comb electrode 310, through the skin and to the comb electrode 305. In this embodiment, the current passing through the comb electrodes 305 and 310 is between 50 μA and 600 μA. Therefore, any voltage can serve as the voltage V1, V3 or V4, as long as the voltage is capable of causing a current of between 50 μA and 600 μA. In one embodiment, the current of the electrode 115 relates to the number of electrodes of the comb electrodes 305 and 310. For example, when the number of electrodes of the comb electrodes 305 and 310 is more, the current passing through the comb electrodes 305 and 310 is larger.

Figure 6A:
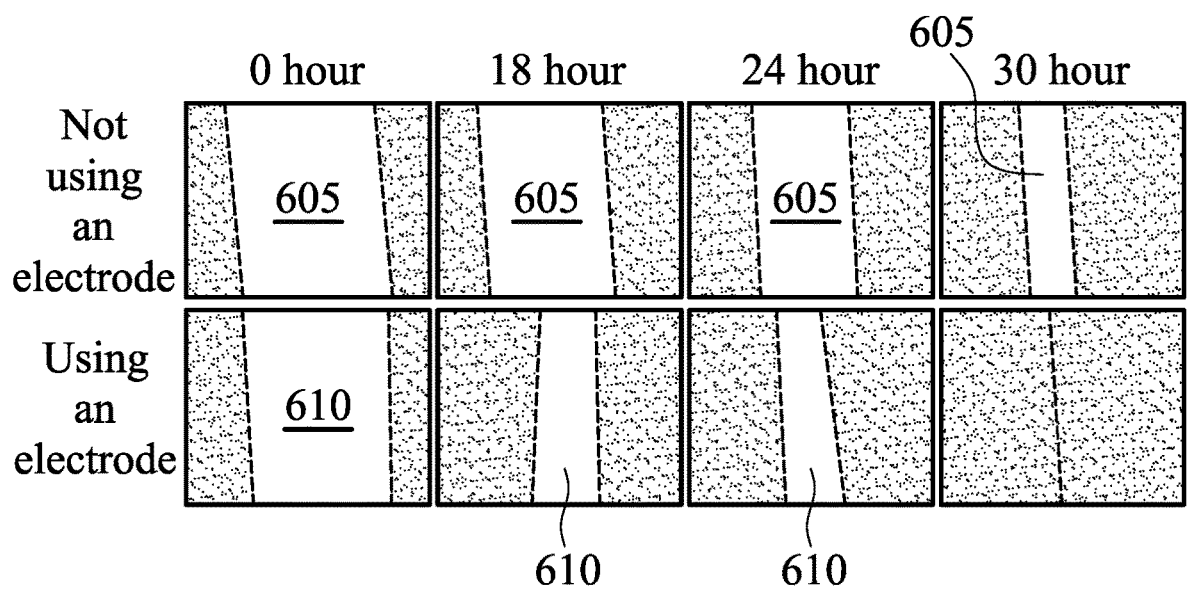
FIG. 6A is a schematic diagram of a wound restoration of using and not using an electrode.
Figure 6B:
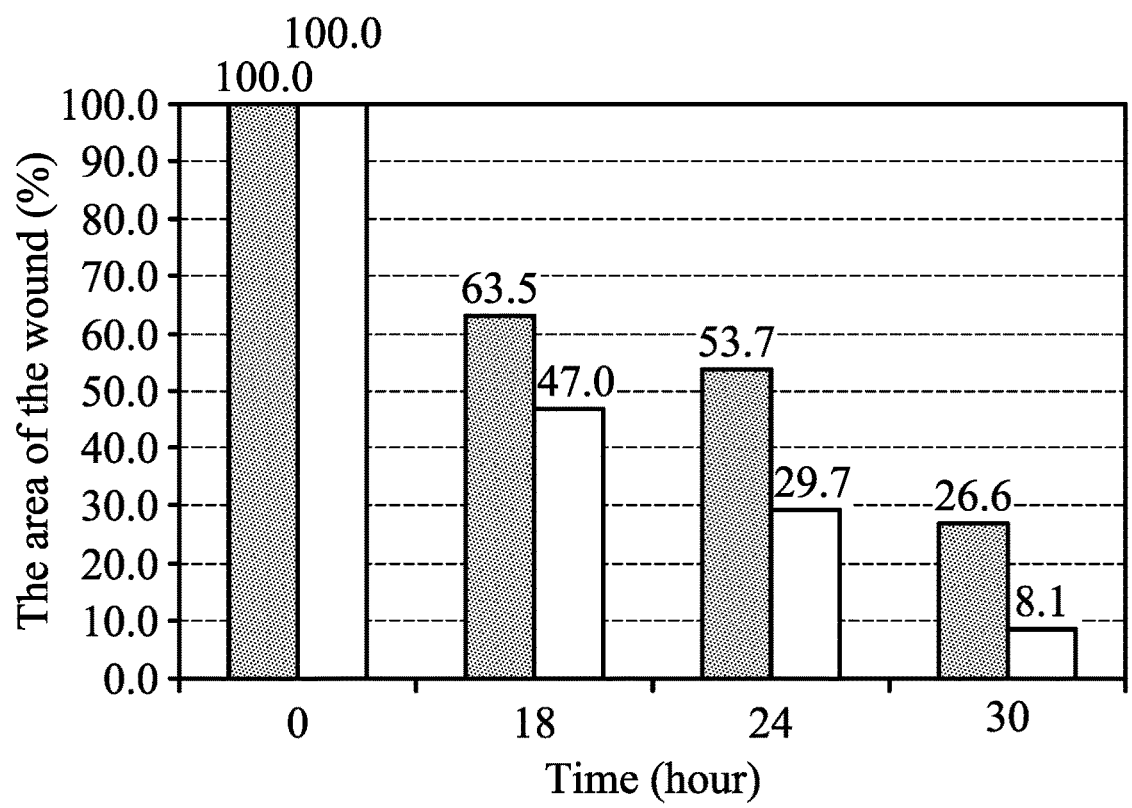
FIG. 6B is an area ratio diagram of a wound.

FIG. 6A is a schematic diagram of a wound restoration of using and not using an electrode. The area of the wound 605 is the same as the area of the wound 610 from the beginning. After 18 hours, the area of the wound 610 is obviously less than the area of the wound 604, wherein no electrode is utilized to the wound 604. FIG. 6B is an area proportion diagram of the wounds 605 and 610. As shown in FIG. 6B, in the 18th hour, the area of the wound 605 is about 63.5% and the area of the wound 610 is about 47.0%. In the 24th hour, the area of the wound 605 is about 53.7% and the area of the wound 610 is about 29.7%. In 30th hour, the area of the wound 605 is about 26.6% and the area of the wound 610 is about 8.1%. Therefore, when the electrical stimulation is applied to the wound, the regeneration speed of the skin cells is increased.

Figure 7:
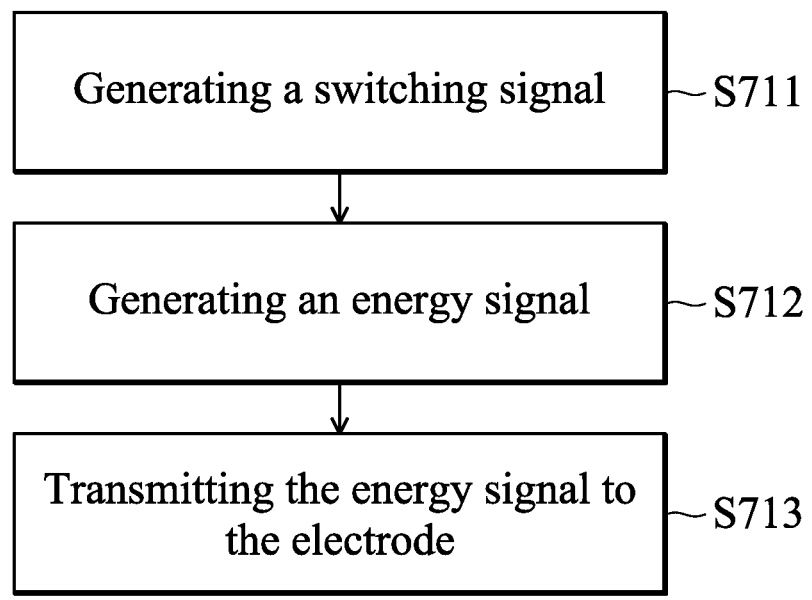
FIG. 7 is a flowchart schematic diagram of an exemplary embodiment of a control method according to various aspects of the present disclosure.

FIG. 7 is a flowchart schematic diagram of an exemplary embodiment of a control method according to various aspects of the present disclosure. The control method is to stimulate the skin cells of a living body to activate the regeneration of the cells to increase the restoration speed of the wound. First, a switching signal is generated (step S711). In one embodiment, the switching signal is generated by a pulse generator or a frequency generator. The pulse generator or the frequency generator sets the duty cycle of the switching signal according to a set signal.

An energy signal is generated according to the switching signal (step S712). In one embodiment, step S712 is to acquire the energy stored in an energy storage element and transfer the acquired energy to generate the energy signal. In other embodiments, step 712 is to charge the energy storage element according to the switching signal. In some embodiments, step 712 is to acquire the body temperature of a living body to generate a charge signal and charge the energy storage element according to the charge signal.

In one embodiment, when the switching signal is at a first level, the energy signal is equal to a first voltage. When the switching signal is at a second level, the energy signal is equal to a second voltage. The first level is opposite to the second level. For example, when the first level is at a high level, the second is at a low level. When the first level is at a low level, the second level is at a high level. In this embodiment, the duration when the energy signal is equal to the first voltage is about 15 minutes, and the duration when the energy signal is equal to the second voltage is between 2.5 hours and 24 hours.

An electrode is utilized to transmit the energy signal to the skin of the living body (step S713). In one embodiment, the electrode is a thermoelectric dressing electrode. In another embodiment, the electrode comprises a first comb electrode and a second comb electrode. The first comb electrode receives the energy signal and comprises a plurality of first electrodes. The first electrodes are electrically connected to each other and extend in a first direction. The second comb electrode receives a ground voltage GND and comprises a plurality of second electrodes. The second electrodes are electrically connected to each other and extend in a second direction. In one embodiment, the first direction is opposite to the second direction. In this embodiment, the first electrodes and the second electrodes are arranged in a staggered manner and are electrically insulated from each other. In one embodiment, when the energy signal is equal to the first voltage, a current passes through the first and second comb electrodes, wherein the current is between 50 µA and 600 µA. In one embodiment, the strength of the current relates to the distance between the two comb electrodes, the duration when the energy signal is applied to the electrode, the body temperature of the living body. In one embodiment, when the difference between the body temperature of the living body and the environment temperature is 7° C. and the distance between the electrodes is 100 µm, the current is about 60 µA and the power-on time is 15 minutes, the restoration speed of the wound is increased.

When the electrode contacts to the wound of the living body, the electrical stimulation is applied to activate the regeneration speed of the cells to increase the restoration speed of the wound. Furthermore, the feature of thermoelectric material is utilized to acquire energy from the surface body temperature of the living body to charge the energy storage element to achieve the therapy capability of the trauma for a long time.

Control methods, or certain aspects or portions thereof, may take the form of a program code (i.e., executable instructions) embodied in tangible media, such as floppy diskettes, CD-ROMS, hard drives, or any other machine-readable storage medium, wherein, when the program code is loaded into and executed by a machine such as a computer, the machine thereby becomes an apparatus for practicing the methods. The methods may also be embodied in the form of a program code transmitted over some transmission medium, such as electrical wiring or cabling, through fiber optics, or via any other form of transmission, wherein, when the program code is received and loaded into and executed by a machine such as a computer, the machine becomes an apparatus for practicing the disclosed methods. When implemented on a general-purpose processor, the program code combines with the processor to provide a unique apparatus that operates analogously to application-specific logic circuits.

Unless otherwise defined, all terms (including technical and scientific terms) used herein have the same meaning as commonly understood by one of ordinary skill in the art to which this present disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

While the present disclosure has been described by way of example and in terms of the preferred embodiments, it is to be understood that the present disclosure is not limited to the disclosed embodiments. On the contrary, it is intended to cover various modifications and similar arrangements (as would be apparent to those skilled in the art). For example, it should be understood that the system, device and method may be realized in software, hardware, firmware, or any combination thereof. Therefore, the scope of the appended claims should be accorded the broadest interpretation so as to encompass all such modifications and similar arrangements.

What is claimed is:

1. An electrical stimulation control circuit comprising:
    a pulse generator configured to generate a switching signal;
    a processing circuit generating an energy signal according to the switching signal; and
    an electrode configured to contact the skin of a living body and comprising:
    a first comb electrode receiving the energy signal and comprising a plurality of first electrodes, wherein the first electrodes are electrically connected to each other and extend in a first direction;
    a second comb electrode receiving a ground voltage and comprising a plurality of second electrodes, wherein the second electrodes are electrically connected to each other and extend in a second direction opposite to the first direction; and
    a thermoelectric generator configured to contact the living body and to generate a charge signal,
    wherein the first electrodes and the second electrodes are arranged in a staggered manner and are electrically insulated from each other, and
    wherein the processing circuit comprises:

an energy storage element; and
a power circuit acquiring energy from the energy storage element to generate the energy signal, wherein the power circuit charges the energy storage element according to the charge signal,
wherein the thermoelectric generator comprises:
a first terminal;
a second terminal configured to contact the living body;
a n-type semiconductor material disposed between the first terminal and the second terminal; and
a p-type semiconductor material disposed between the first terminal and the second terminal,
wherein responsive to a temperature difference between the first terminal and the second terminal reaching a predetermined value, a current passes between the first terminal and the second terminal and is provided to the charge signal.

2. The electrical stimulation control circuit as claimed in claim 1, wherein during a first period, the energy signal is equal to a first voltage, during a second period, the energy signal is equal to a second voltage, the first voltage is higher than the second voltage, the duration of the first period is 15 minutes, and the duration of the second period is between 2.5 hours and 24 hours.

3. The electrical stimulation control circuit as claimed in claim 2, wherein when the electrode is attached to the skin of a living body and the energy signal is equal to the first voltage, a current passes through the first comb electrode, the skin of the living body and the second comb electrode, and the current is between 50 µA and 600 µA.

4. The electrical stimulation control circuit as claimed in claim 1, wherein the energy storage element is a lithium ion capacitor, a supercapacitor or a battery.

5. The electrical stimulation control circuit as claimed in claim 1, wherein the power circuit charges the energy storage element according to the switching signal.

6. The electrical stimulation control circuit as claimed in claim 1, wherein the power circuit comprises a single-inductor multiple-input-multiple-output circuit.

7. The electrical stimulation control circuit as claimed in claim 1, wherein the power circuit comprises:
a first converter charging the energy storage element according to the charge signal; and
a second converter acquiring the energy from the energy storage element according to the switching signal to generate the energy signal.

8. The electrical stimulation control circuit as claimed in claim 1, wherein the power circuit comprises:
a first converter charging the energy storage element according to the charge signal;
a second converter acquiring the energy from the energy storage element to generate the energy signal; and
a switch coupled between the second converter and the electrode and transmitting the energy signal to the electrode according to the switching signal.

9. The electrical stimulation control circuit as claimed in claim 1, wherein the power circuit comprises:
a capacitor receiving the switching signal;
a first switch having a first terminal coupled to the capacitor and further having a second terminal;
a second switch having a first terminal coupled to the second terminal of the first switch and further having a second terminal coupled to the energy storage element;
a third switch having a first terminal coupled to the second terminal of the second switch and the energy storage element, and further having a second terminal;
a fourth switch having a first terminal coupled to the second terminal of the first switch and further having a second terminal;
a fifth switch having a first terminal coupled to the second terminal of the fourth switch and further having a second terminal coupled to the second terminal of the third switch, wherein the second terminal of the fourth switch and the first terminal of the fifth switch are grounded;
a sixth switch having a first terminal coupled to the second terminal of the third switch and further having a second terminal coupled to the electrode;
an inductor having a first terminal coupled to the second terminal of the first switch, the first terminal of the second switch, and the first terminal of the fourth switch, wherein the inductor further has a second terminal coupled to the second terminal of the third switch, the second terminal of the fifth switch, and the first terminal of the sixth switch.

10. The electrical stimulation control circuit as claimed in claim 1, wherein:
responsive to the temperature difference between the first terminal and the second terminal reaching the predetermined value, the holes in the p-type semiconductor material are moved toward a first specific terminal of the first terminal and the second terminal and the electrons in the n-type semiconductor material are moved toward a second specific terminal of the first terminal and the second terminal, and
the temperature of the first specific terminal is lower than the temperature of the second specific terminal.

11. The electrical stimulation control circuit as claimed in claim 10, wherein the power circuit transfers the current passing between the first terminal and the second terminal to generate a transferred current and provides the transferred current to the energy storage element.

12. A control method for stimulating skin cells of a living body, comprising:
generating a switching signal;
acquiring energy stored in an energy storage element according to the switching signal;
converting the energy stored in the energy storage element to generate an energy signal;
transmitting the energy signal to the skin of the living body via an electrode, wherein the electrode comprises:
a first comb electrode receiving the energy signal and comprising a plurality of first electrodes, wherein the first electrodes are electrically connected to each other and extend in a first direction; and
a second comb electrode receiving a ground voltage and comprising a plurality of second electrodes, wherein the second electrodes are electrically connected to each other and extend in a second direction opposite to the first direction, wherein the first electrodes and the second electrodes are arranged in a staggered manner and are electrically insulated from each other; and
generating a charge signal, by a thermoelectric generator, to charge the energy storage element,
wherein the thermoelectric generator comprises:
a first terminal;
a second terminal configured to contact the living body;
a n-type semiconductor material disposed between the first terminal and the second terminal; and
a p-type semiconductor material disposed between the first terminal and the second terminal,
wherein responsive to a temperature difference between the first terminal and the second terminal reaching a predetermined value, a current passes between the first terminal and the second terminal and is provided to the charge signal.

13. The control method as claimed in claim 12, wherein during a first period, the energy signal is equal to a first voltage, during a second period, the energy signal is equal to a second voltage, the first voltage is higher than the second voltage, the duration of the first period is 15 minutes, and the duration of the second period is between 2.5 hours and 24 hours.

14. The control method as claimed in claim 12, wherein when the electrode is attached to the skin of the living body and the energy signal is equal to the first voltage, a current passes through the first comb electrode, the skin of the living body and the second comb electrode, and the current is between 50 μA and 600 μA.

15. The control method as claimed in claim 12, further comprising:

charging the energy storage element according to the switching signal.

\* \* \* \* \*